(12) United States Patent
Prasad

(10) Patent No.: US 6,498,145 B1
(45) Date of Patent: Dec. 24, 2002

(54) USE OF PURIFIED SDG AS A HYPOTENSIVE (VASODILATOR) AGENT

(75) Inventor: Kailash Prasad, Saskatoon (CA)

(73) Assignee: University of Saskatchewan Technologies Incorporated, Saskatoon (CA)

( * ) Notice: Subject to any disclaimer, the term of this patent is extended or adjusted under 35 U.S.C. 154(b) by 0 days.

(21) Appl. No.: 09/593,401

(22) Filed: Jun. 14, 2000

(51) Int. Cl.[7] .................. A01N 61/00; A01N 43/04; A61K 31/70
(52) U.S. Cl. .............................. 514/25; 514/1
(58) Field of Search ..................... 514/1, 25

(56) References Cited

U.S. PATENT DOCUMENTS

| | | | |
|---|---|---|---|
| 5,837,256 A | 11/1998 | Clark et al. | 424/195.1 |
| 5,846,944 A | 12/1998 | Prasad | 514/25 |

OTHER PUBLICATIONS

Talom et al, High Flaxseed (Linseed) Diet . . . , 1999, vol. 64, No. 16 pp. 1415–1425.*

Klosterman et al., "The Constitution of Linocinnamarin[1]", Contribution From The Department of Agricultural Chemistry, North Dakota Agricultural Experiment Station, and Department of Agricultural Biochemistry, University of Minnesota, vol. 77, pp. 420 and 421, Jul. 29, 1954.

Klosterman et al., "The Glucosides of Flaxseed. II. Linocaffein[1]", Contribution From The Department of Agricultural Chemistry, North Dakota Agricultural College, vol. 81, pp. 2188–2191, Sep. 25, 1958.

Klosterman et al., "The Constitution of Linocinnamarin", Contribution From The Department of Chemistry, North Dakota Agricultural Experiment Station, and Department of Agricultural Biochemistry, University of Minnesota, vol. 77, pp. 420 and 421, Jul. 29, 1954.

Bambagiotti–Alberti et al., "Revealing the Mammalian Lignan Precursor Secoisolariciresinol Diglucoside in Flax Seed by Ionspray Mass Spectrometry", Rapid Communications in Mass Spectrometry, vol. 8, pp. 595–598 (1994).

Harris et al., "Assays for Potentially Anticarcinogenic Phytochemicals in Flaxseed", Cereal Foods World, vol. 38, No. 3, pp. 147–151, Mar. 1993.

MacRae et al., "Biological Activities of Lignans", Phytochemistry, vol. 23, No. 6, pp. 1207–1220, 1984.

Klosterman et al., "The Isolation of β–Hydroxy–β–methylglutaric Acid from the Seed of Flax", Contribution from the Department of Agricultural Chemistry, North Dakota Agricultural Experiment . . . Agricultural biochemistry, University of Minnesota, vol. 76, pp. 1229 and 1230, Aug. 24, 1953.

\* cited by examiner

*Primary Examiner*—Jezia Riley
(74) *Attorney, Agent, or Firm*—Norris M. Eades

(57) ABSTRACT

The compound secoisolariciresinol diglucoside (SDG), obtained from flaxseed is used for treating hypertension or for reducing or preventing the development of elevated blood pressure in humans or animals. These uses include the treatment of ischemic heart disease, heart failure and intermittent claudication.

3 Claims, 9 Drawing Sheets

USE OF PURIFIED SDG AS A HYPOTENSIVE (VASODILATOR) AGENT

BACKGROUND OF THE INVENTION

This invention relates to the use of purified SDG (secoisolariciresinol diglucoside) as a hypotensive (vasodilator) agent in treating hypertension or reducing or preventing the development of elevated blood pressure.

Hypertension is one of the leading causes of deaths in this society. According to a survey done between 1986–1992, the overall prevalence of hypertension in the Canadian population was 22% and was higher in men (26%) than in women (18%). There is overwhelming evidence that elevated systolic or diastolic blood pressure or both, increases the probability of ischemic heart disease, stroke, atherosclerosis and overall mortality. The causes of death in hypertensive are heart failure (45%), heart attack (35%), stroke (15%) and kidney failure (5%). Treatment and control of high blood pressure reduce the risk of ischemic heart disease and stroke. Ischemic heart disease is the leading cause of death and hospitalization.

The present treatments of hypertension and ischemic heart disease have side effects and are expensive. The drugs used for treating hypertension include diuretics, antiadrenergic agents, vasodilator, central agonists, angiotensin converting enzyme inhibitors, calcium channel blockers, and angiotensin II receptor antagonists.

Diuretics reduce blood potassium, increase serum cholesterol, LDL-cholesterol and triglycerides, are diabetogenic, and produce gout. Beta-adrenergic blockers produce insomnia, fatigue, sexual dysfunction and exacerbation of asthma, increases serum cholesterol and triglycerides, and produce cold hands. Angiotensin converting enzyme inhibitors could cause cough, angioedema, urticaria and loss of white blood and other blood cells. Calcium channel blockers produce flushing, headaches, palpitation and swelling of ankles.

For treatment of ischemic heart disease (angina pectoris, myocardial infarction) the physiologic basis of treatment with drugs are to reduce oxygen demand and increase oxygen supply. For this purpose, the vasodilator (nitrites and nitrates), beta-adrenergic blocker, calcium channel blockers are generally being used.

Nitrites and nitrates produce headache, flushing face, and reflex tachycardia. Reflex tachycardia would increase the oxygen consumption of the heart and hence would counteract to some extent the beneficial effect of nitrites and nitrates in ischemic heart disease. Also nitrites and nitrates produce tolerance.

The drugs used for the treatment of hypertension and ischemic heart disease are also very expensive. Side effects common to drugs, especially antihypertensive drugs, together with high cost of the drugs, have always been a major cause of noncompliance and concern. It is particularly difficult to accept treatment-related symptoms for a life-long disease, especially hypertension. For example, a research conducted by J. Menard [Improving hypertension treatment. Where should we put our efforts: new drugs, new concepts, or new management? (1992) Am. J. Hypertens. 5(12 Pt 2): 252S–258S] revealed that current treatment failure is frequent and side effects are common. The results showed that in the systolic hypertension in the elderly program, 28 to 35% of patients did not reach the goal blood pressure, 13% stopped treatment because of side effects, and 21% required medication other than a diuretic and a beta-blocker.

Therefore, despite the availability of numerous antihypertensive agents, a concerted research effort to develop new approaches to hypertension treatment is necessary.

Prasad, U.S. Pat. No. 5,846,944 describes the use of purified SDG for the treatment of hypercholesterolemic atherosclerosis and for reducing total cholesterol, as well as for the treatment of diabetes mellitus. Atherosclerosis is lipid deposit in the arteries and hence narrowing of blood vessels, resulting in ischemic heart disease.

The literature also describes the beneficial effect of flaxseed to reduce ascites and pulmonary hypertension in broiler chickens [J. Bond et al. (1996) Effect of dietary flax oil and hypobaric hypoxia on right ventricular hypertrophy and ascites in broiler chickens. British Poultry Science 37(4): 731–741]. Researchers have also inferred a role for flax in diet of patients with ischemic heart disease, hyperlipidemia and high blood pressure. [I. A. Rozanova et al. (1997) Effect of antiatherosclerotic diet, containing polyunsaturated fatty acids of the omega-3 family from flax oil, on fatty acid composition of cell membranes of patients with ischemic heart disease. Vopr. Pitan. (5): 15–17]. It has been shown that alpha-linolenic acid has a beneficial effect in coronary heart disease, hypertension, and inflammatory disorders [E. Mantzioris et al. (1995) Differences exist in the relationships between dietary linoleic and alpha-linolenic acids and their respective long-chain metabolites. Am. J. Clin. Nutr. 61(2): 320–324]. Yet, little is known about the hypotensive effect of the lignan components of flaxseed. Moreover, use of whole flaxmeal or oil components of flaxseed has been found to result in progressive weight gain due to the high caloric value of the oil components.

Flaxseed is known to contain a myriad of molecules including lignan and oil fractions. Secoisolariciresinol diglucoside (SDG) is the principal lignan from flaxseed.

Although flaxseed has been used as an edible grain in different parts of the world since ancient times, use of flaxseed was limited due to the presence of cyanogenic glucosides and diglucosides in the seeds as they may release cyanide upon hydrolysis. Also, flaxseed has to be used in large quantity to be effective.

In Westcott and Muir U.S. Pat. No. 5,705,618, issued January, 1998, there is described a practical method of extracting and purifying SDG. By this technique, SDG can be obtained in a purity of greater than 95%.

The purpose of the present invention is to provide a method of using flaxseed for medical purposes without the aforementioned drawbacks of cyanogenic glycosides, and caloric loads. SDG compound is obtained from natural food product (flaxseed), and hence it is expected to have non or minimal side effect if any. It is also an inexpensive drug as compared to other conventional drugs used in the treatment of hypertension and ischemic heart disease.

SUMMARY OF THE INVENTION

In accordance with this invention, it has been found that by administering SDG from flaxseed in substantially pure form to a human or non-human animal, elevated blood pressure can be reduced and hypertension can be prevented. The SDG serves to lower blood pressure by dilation of blood vessels. Its vasodilator (hypotensive) effect appears to be mediated primarily through the inhibition of guanylate cyclase, partly through inhibition of angiotensin I converting enzyme and blockade of angiotensin II receptor, and through histamine.

SDG is also useful for the treatment of ischemic heart disease (coronary artery disease) where the SDG serves to dilate the coronary blood vessels to supply more blood to the heart muscle. This abolishes ischemia of the heart and hence abolishes or prevents chest pain and other signs and symptoms associated with an ischemic heart. Also, by reducing the afterload (aortic pressure) because of lowering blood pressure, SDG serves to decrease the myocardial oxygen consumption thereby reducing ischemia of the heart.

A further associated use of SDG is for treating intermittent claudication, which is a leg pain while walking due to narrowing of the blood vessels of a leg muscle. Decreased blood flow to the leg muscle initiates the pain. SDG by dilating blood vessels increases the blood supply to the leg muscle and relieves the leg pain.

A still further associated use of SDG is for the treatment of heart failure, where it serves to reduce the afterload to the heart by lowering blood pressure. Thus, the heart is able to work against low arterial pressure thereby increasing the cardiac output.

Diabetic patients are known to suffer hypertension and SDG is effective in lowering the blood pressure of hypertensive patients with diabetes.

Unlike the uses of SDG described in U.S. Pat. No. 5,846,944, in the uses according to the present invention the SDG acts primarily to dilate blood vessels. This is achieved without the undesirable side effects of cyanogenic glycosides and caloric loads.

The SDG is preferably used at a high degree of purity of over 90%, with a purity of over 95% being the preferred. It can be administered orally, intraperitoneally or intravenously. It has been found to be highly effective in normotensives when given intravenously in the doses of 10–30 mg/kg body weight and in hypertensives when given intravenously in the doses of 1–15 mg/kg body weight, intraperitoneally in the doses of 5–200 mg/kg body weight, and orally in the dose of 100 mg/kg body weight. The oral doses may conveniently be in the form of tablets or capsules and the SDG may be used together with a variety of pharmaceutically cceptable diluents or carriers.

DESCRIPTION OF THE PREFERRED EMBODIMENTS

EXAMPLE 1

The effects of SDG in the doses of 10 mg, 15 mg, 20 mg and 30 mg/kg given intravenously were investigated on the blood pressure (B.P.) and heart rate of anesthetized normotensive rats. The number of rats used were 8, 3, 9, and 3 respectively for the doses of SDG (10 mg, 15 mg, 20 mg and 30 mg/kg body wt.). The effects of various doses of SDG on mean, systolic and diastolic blood pressures and heart rate are summarized in FIGS. 1–4. The maximum fall in mean B.P. were approximately 38%, 29%, 46% and 57% with 10 mg, 15 mg, 20 mg and 30 mg/kg dose of SDG respectively at 15 minutes after administration of SDG. After 15 minutes the blood pressure tended to recover but the recovery was not complete. The mean blood pressure at the end of three hours after SDG administration were approximately 25% lower than control values. The changes in the systolic and diastolic pressure were similar to the mean blood pressure with various doses of SDG. These results suggest that SDG has hypotensive effect and that this effect is of long duration. One would expect a very long duration of hypotensive effect when SDG is given orally.

Figure 2:
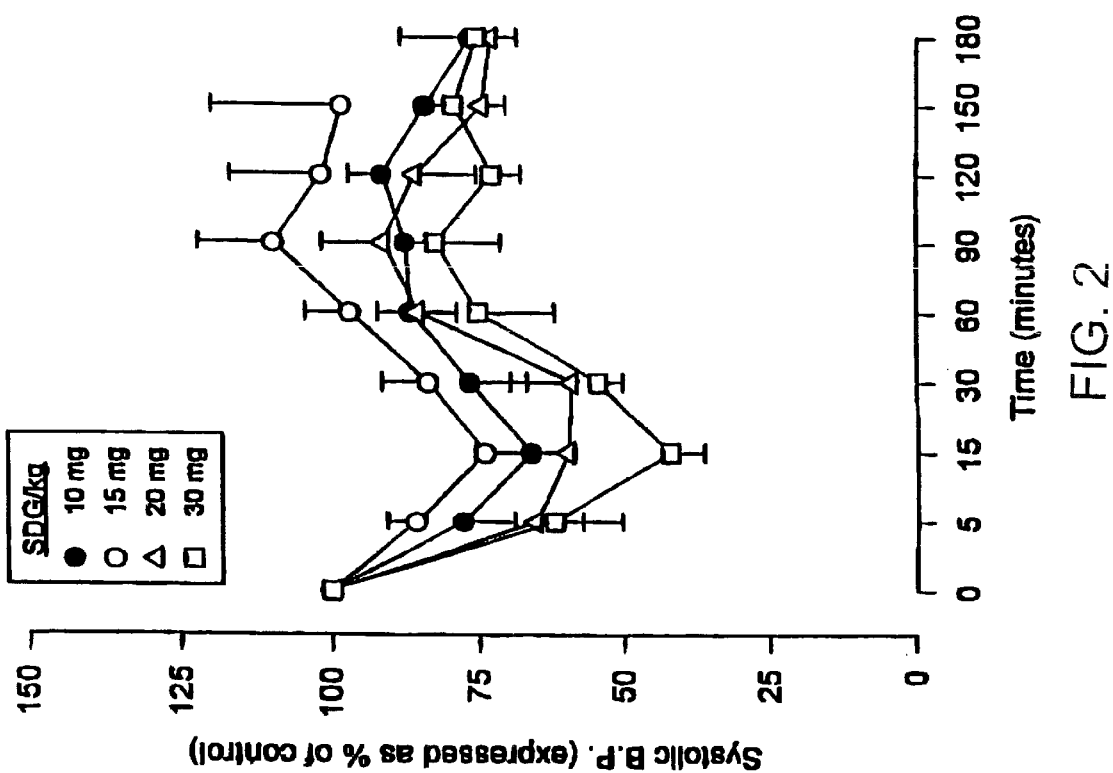
FIG. 2 is a graph showing effects of four doses of SDG on the mean systolic blood pressure (B.P.) in anesthetized normotensive rats; the results are expressed as mean±S.E.
Figure 1:
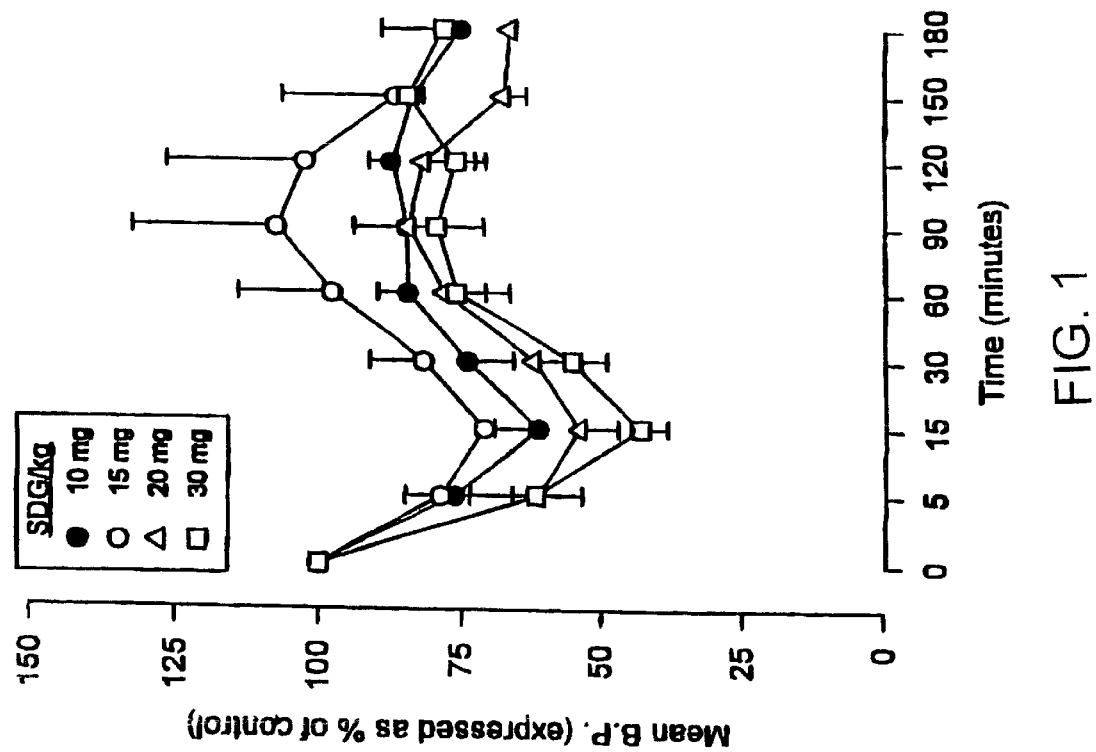
FIG. 1 is a graph showing effects of four doses of SDG on the mean arterial blood pressure (B.P.) in anesthetized normotensive rats; the results are expressed as mean±S.E.
Figure 4:
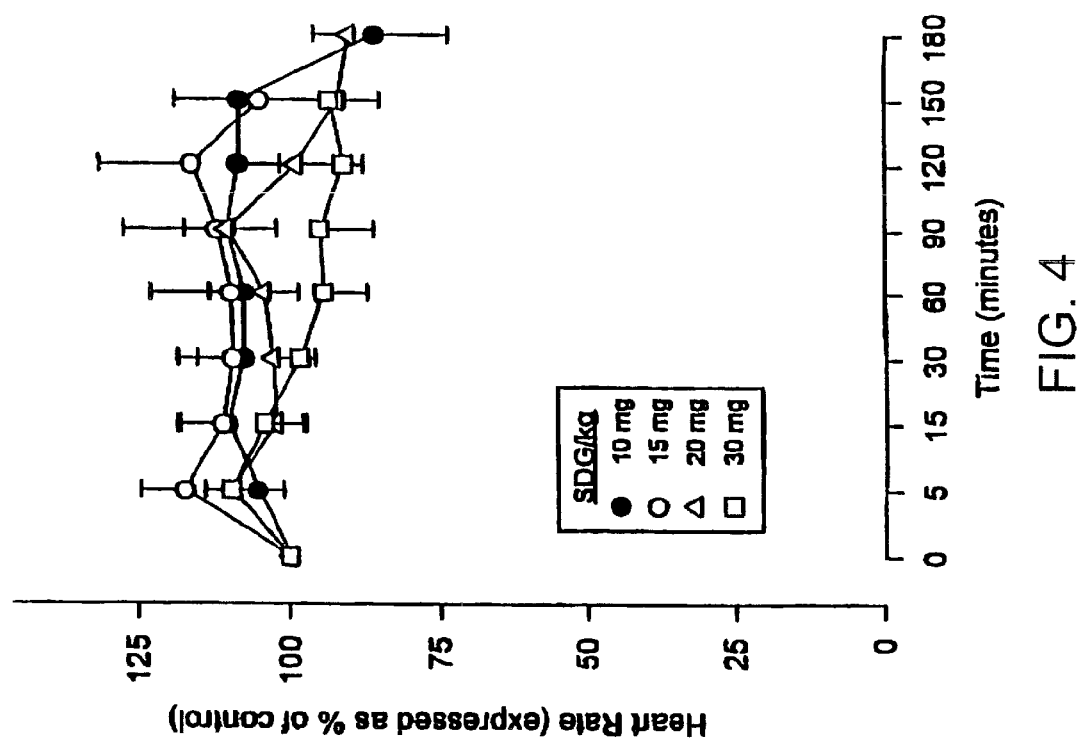
FIG. 4 is a graph showing effects of four doses of SDG on the heart rate in anesthetized normotensive rats; results are expressed as mean±S.E.
Figure 3:
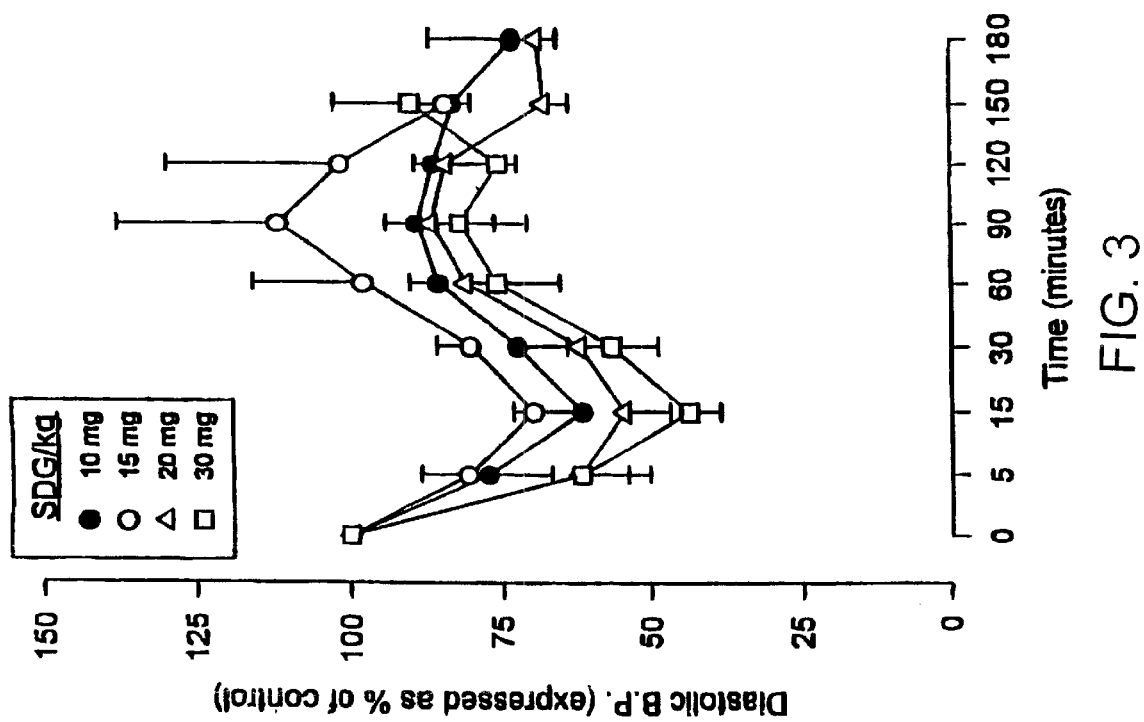
FIG. 3 is a graph showing effects of four doses of SDG on the diastolic blood pressure (B.P.) in anesthetized normotensive rats; results are expressed as mean±S.E.

The heart rate was not significantly altered by any dose of SDG (FIG. 4).

Figure 6:
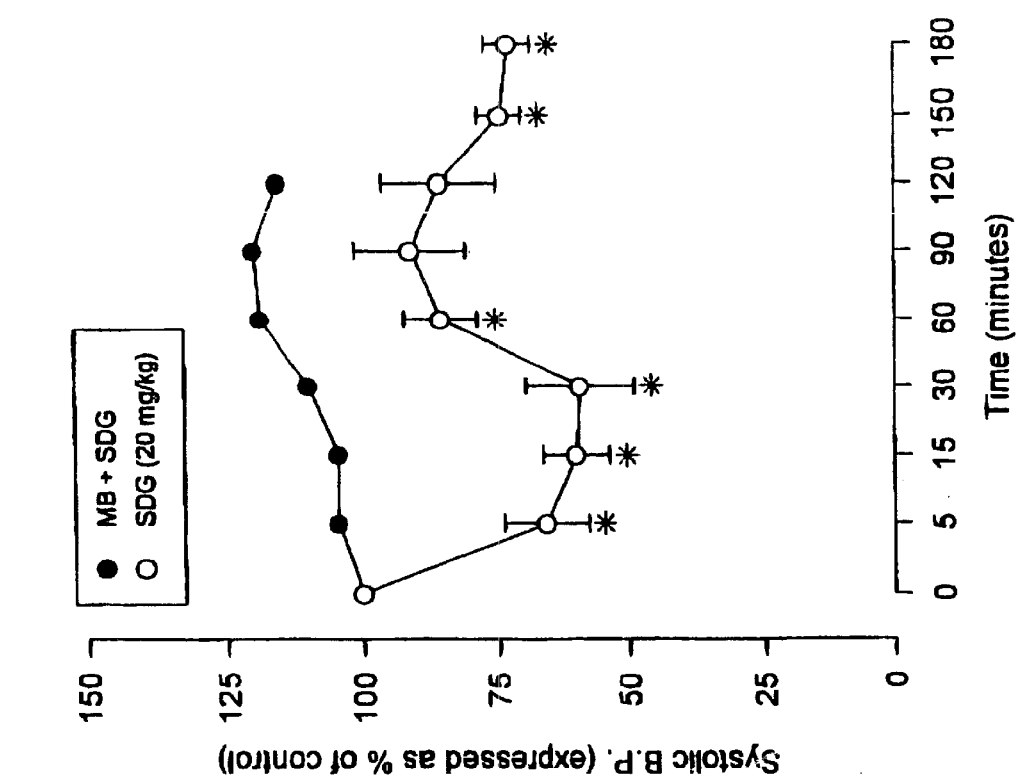
FIG. 6 is a graph showing effects of SDG (20 mg/kg, intravenously) on the systolic blood pressure (B.P.) in the absence or presence of methylene blue (MB) (0.5 mg/kg) in the anesthetized normotensive rats; results are expressed as mean±S.E. $*p<0.05$, comparison of values at various times with respect to "0" time.
Figure 5:
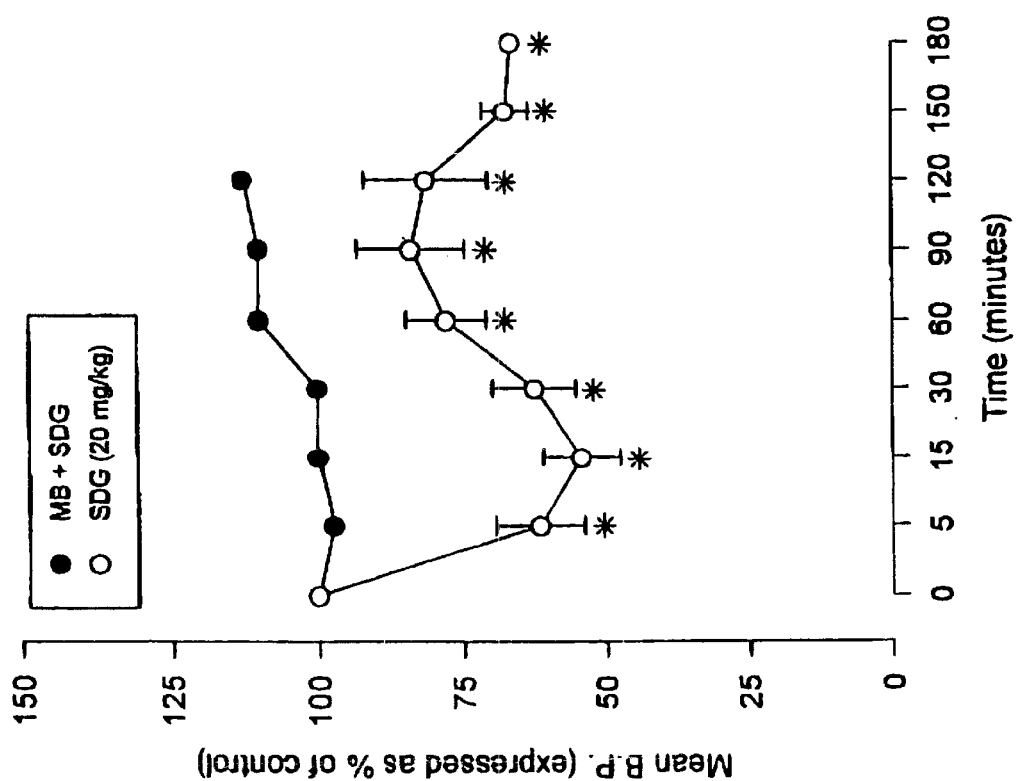
FIG. 5 is a graph showing changes in the mean arterial blood pressure (B.P.) with SDG (20 mg/kg, intravenously) in the absence or presence of methylene blue (MB) (0.5 mg/kg); methylene blue was given 15 minutes prior to administration of SDG and results are expressed as mean±S.E. $*p<0.05$, comparison of values at various times with respect to "0" time.
Figure 8:
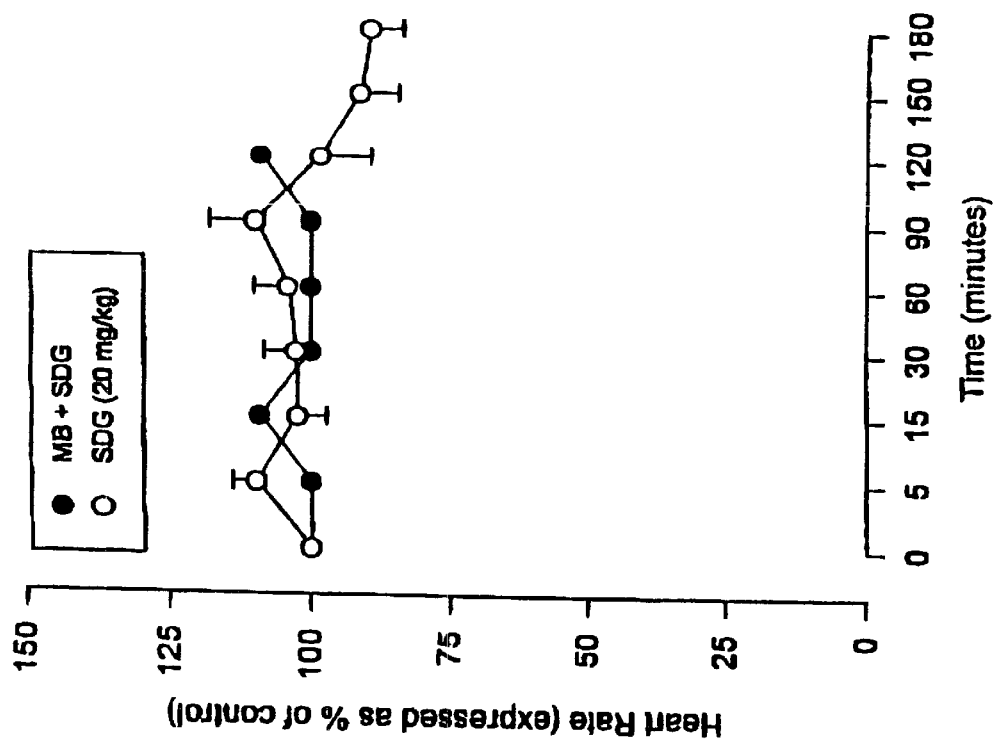
FIG. 8 is a graph showing effects of SDG (20 mg/kg, intravenously) on the heart rate in the absence or presence of methylene blue (MB) (0.5 mg/kg) in anesthetized normotensive rats; results are expressed as mean±S.E.
Figure 7:
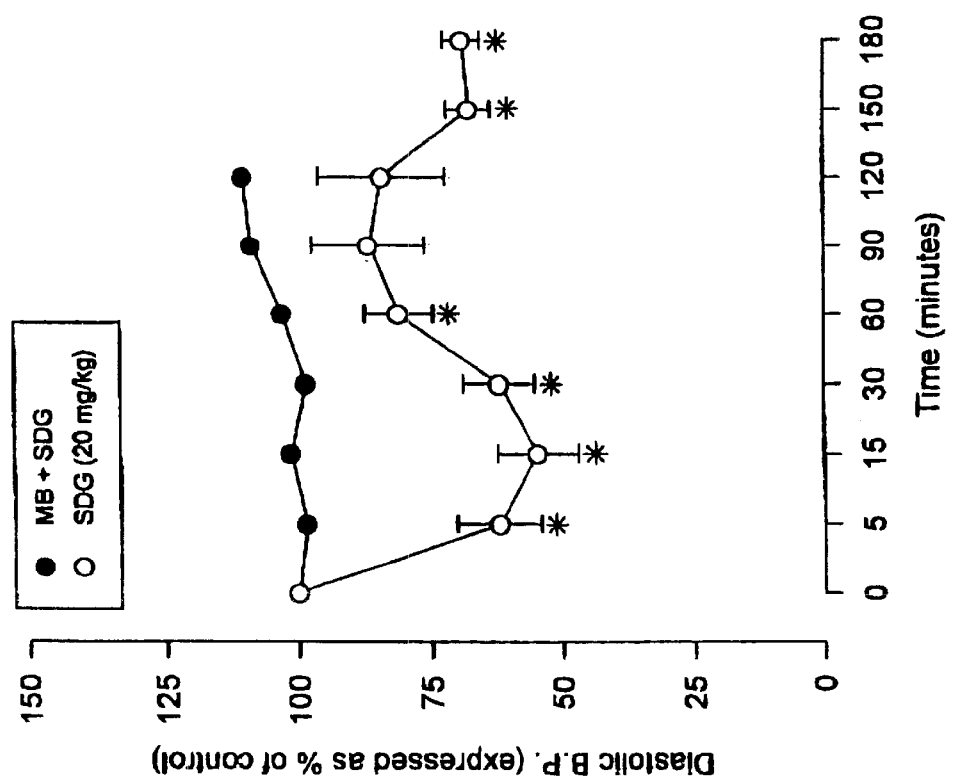
FIG. 7 is a graph showing effects of SDG (20 mg/kg, intravenously) on the diastolic blood pressure (B.P.) in the absence or presence of methylene blue (MB) (0.5 mg/kg) in the anesthetized normotensive rats; results are expressed as mean±S.E. $*p<0.05$, comparison of values at various times with respect to "0" time.
Figure 10:
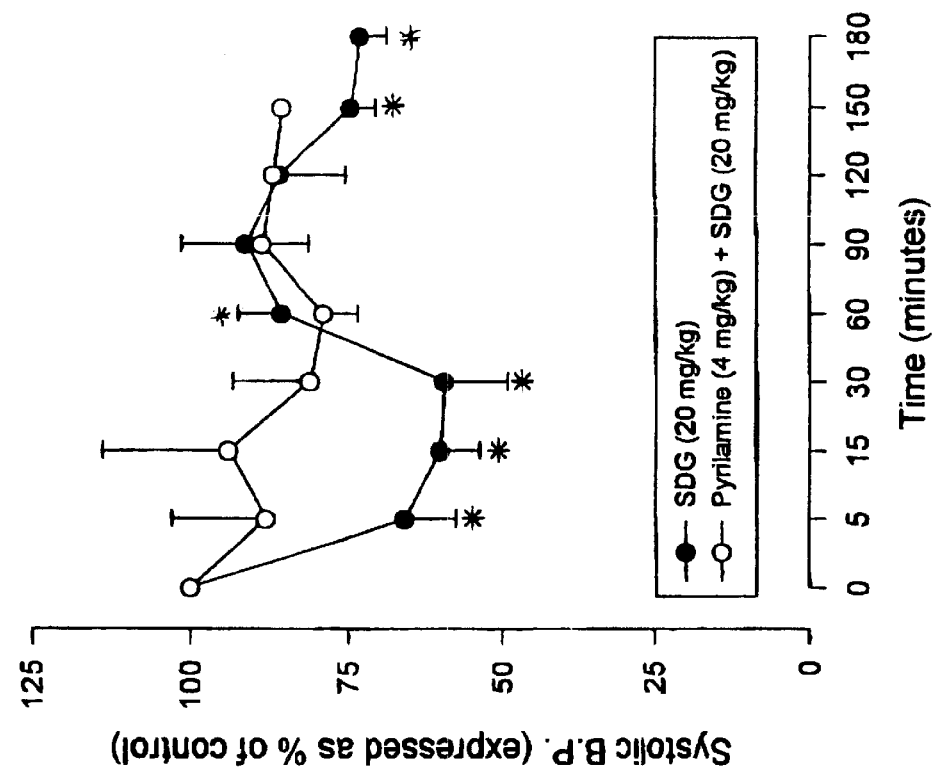
FIG. 10 is a graph showing effects of SDG in the absence or presence of pyrilamine on the systolic blood pressure in anesthetized normotensive rats; results are expressed as mean±S.E. $*p<0.05$, comparison of values at various times with respect to "0" time.
Figure 9:
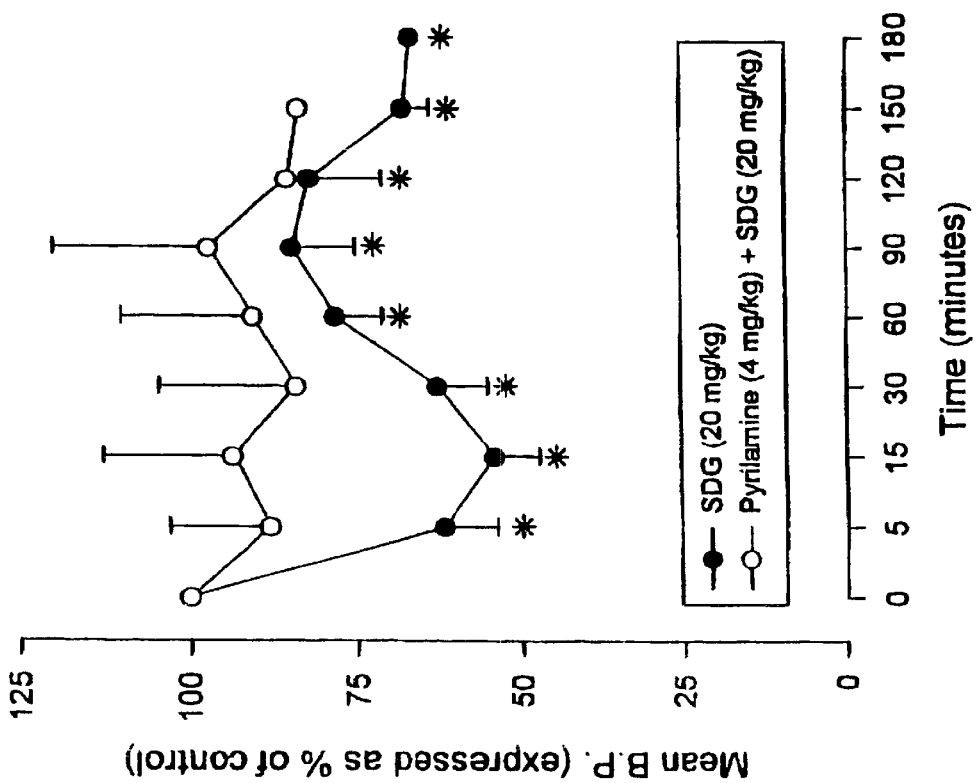
FIG. 9 is a graph showing effects of SDG in the absence or presence of pyrilamine on the mean arterial blood pressure (B.P.) in anesthetized normotensive rats. Pyrilamine was given 15 minutes before administration of SDG. The results are expressed as mean±S.E. $*p<0.05$, comparison of values at various times with respect to "0" time.
Figure 12:
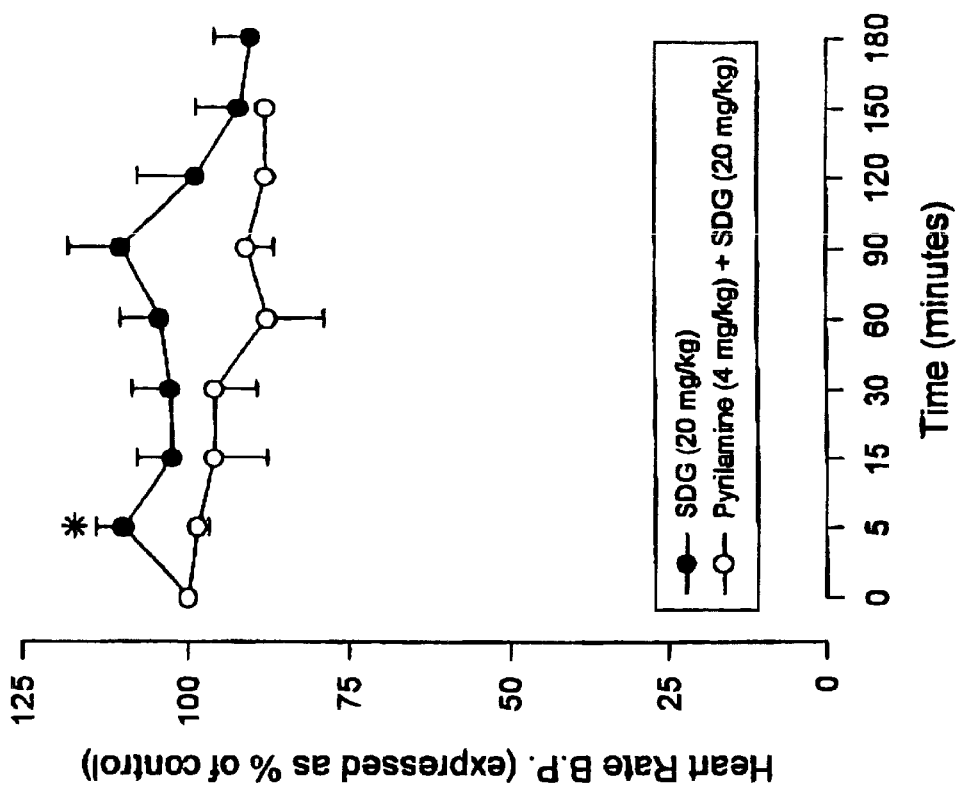
FIG. 12 is a graph showing effects of SDG in the absence or presence of pyrilamine on heart rate in anesthetized normotensive rats; results are expressed as mean±S.E. $*p<0.05$, comparison of values at various times with respect to "0" time.
Figure 11:
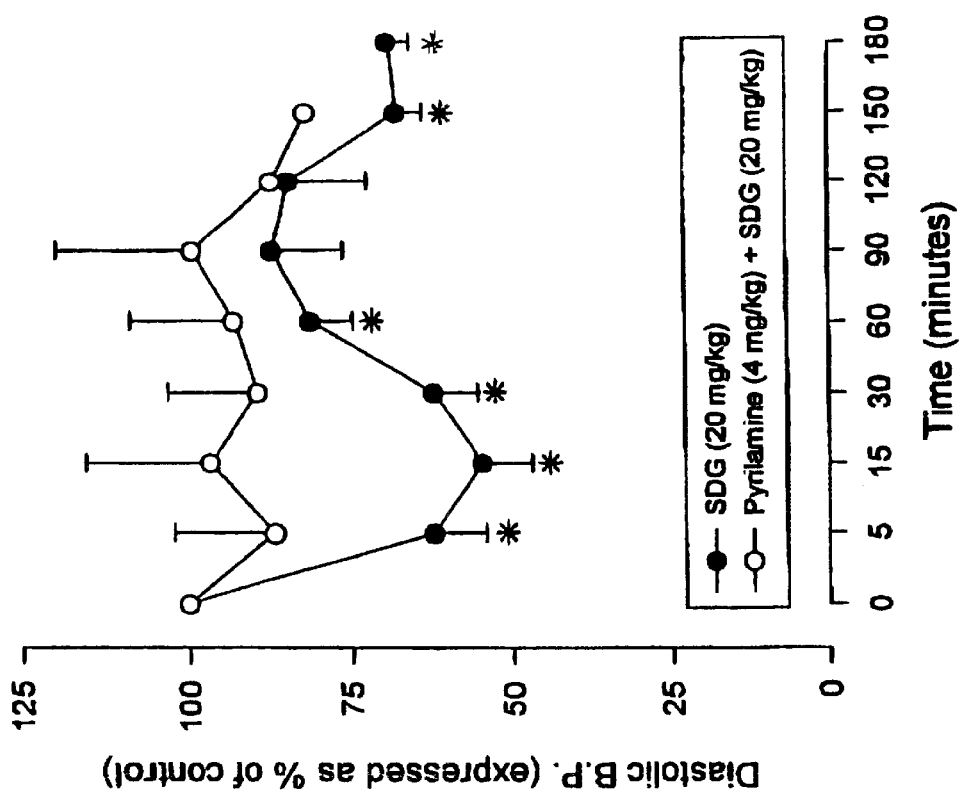
FIG. 11 is a graph showing effects of SDG in the absence or presence of pyrilamine on the diastolic pressure in anesthetized normotensive rats; results are expressed as mean±S.E. $*p<0.05$, comparison of values at various times with respect to "0" time.

Hypotensive effect of SDG was not prevented by premedication with atropine (acetylcholine receptor blocker), $N^G$-monomethyl-L-arginine (an inhibitor of nitric oxide synthase) and indomethacin (an inhibitor cyclooxygenase), suggesting that hypotensive effect of SDG is not mediated by acetylcholine, nitric oxide or arachidonic acid vasodilator metabolites. However the hypotensive effect of SDG was completely prevented by methylene blue (a guanylate cyclase inhibitor) (FIGS. 5–7) suggesting that hypotensive effect of SDG is mediated by guanylate cyclase. Heart rate was not affected by methylene blue (FIG. 8). Hypotensive effect of SDG is also partly prevented by pyrilamine (histamine receptor blocker) (FIGS. 9–11), suggesting the hypotensive effect is mediated partly through histamine. Heart rate was practically unchanged (FIG. 12).

These results indicate that SDG is a hypotensive agent and this effect is not associated with reflex tachycardia. The mechanism of vasodilation (hypotension) is similar to nitrites used in patients with ischemic heart disease.

EXAMPLE 2

Figure 13:
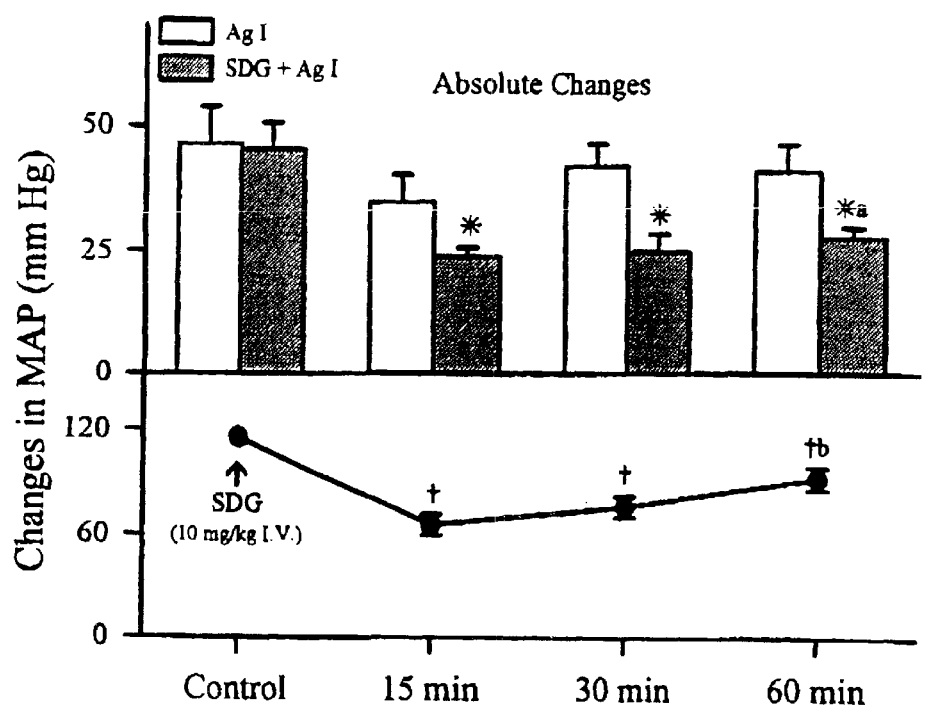
FIG. 13 is a graph showing the effect of angiotensin I (Ag I) on the mean arterial pressure of anesthetized Sprague-Dawley rats in the absence (blank bar) and in the presence of SDG (shaded bar); a line plot shows the effects of SDG (I.V.) on the mean arterial pressure as a function of time and the results are expressed as mean±S.E. $*p<0.05$, comparison of the values at 15 minutes, 30 minutes and 60 minutes with respect to values at control (before any drug treatment). $^a p<0.05$, 15 minutes vs 30 minutes or 60 minutes. $^b p<0.05$, 15 minutes vs 30 minutes or 60 minutes. $^\dagger p<0.05$, control vs all other time-intervals.

Further experiments were conducted to determine if the SDG-induced fall in the blood pressure is mediated through inhibition of angiotensin converting enzyme (ACE). Angiotensin I is converted to angiotensin II which is vasoconstrictor and raises blood pressure. If SDG lowers blood pressure by inhibiting ACE, then SDG would reduce/prevent the angiotensin I-induced rise in the blood pressure. Experiments were conducted in six normotensive Sprague-Dawley rats. The effects of angiotensin I (0.2 µg/kg) given intravenously at various intervals before and after administration of SDG (10 mg/kg) intravenously were observed for 60 minutes. Control effects of angiotensin I were observed for similar duration in the absence of SDG. The results are summarized in FIG. 13. There was a marked reduction in the response of angiotensin I on the mean arterial pressure in SDG-treated rats. However, the effects of angiotensin on arterial pressure of untreated rats remained unaltered. SDG (10 mg/kg) produced a marked fall in the mean arterial pressure. These results indicate that hypotensive effects of SDG is partially mediated through the inhibition of ACE.

EXAMPLE 3

Figure 14:
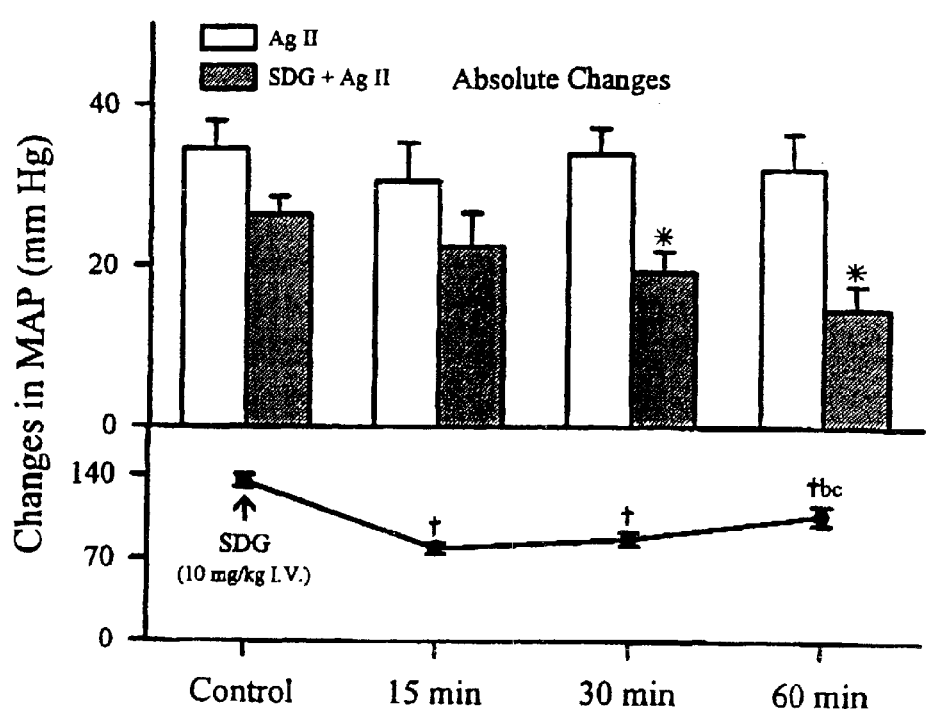
FIG. 14 is a graph showing the effect of angiotensin II on the mean arterial pressure of anesthetized Sprague-Dawley rats in the absence (blank bar) and in the presence of SDG (shaded bar); a line plot shows the effects of SDG on the mean arterial pressure as a function of time and the results are expressed as mean±S.E.
$*p<0.05$, comparison of the values at 15 minutes, 30 minutes and 60 minutes with respect to values at control (before any drug treatment).
$^\dagger p<0.05$, comparison of values at 15 minutes, 30 minutes and 60 minutes with respect to values at control.
$^b p<0.05$, 15 minutes vs 30 minutes or 60 minutes.
$^c p<0.05$, 30 minutes vs 60 minutes.

To determine if the SDG-induced fall in the blood pressure is mediated through the blockade of angiotensin II receptor, experiments were carried out in normotensive Sprague-Dawley rats. Effects of angiotensin II (0.2 µg/kg, I.V.) given before and after 15 minutes, 30 minutes and 60 minutes of SDG (10 mg/kg) administered intravenously were investigated on the arterial pressure of six anesthetized Sprague-Dawley rats. The results are summarized in FIG. 14. Angiotensin II response was moderately reduced in the presence of SDG. The response of angiotensin II on the mean arterial pressure in untreated rats remained unaltered. SDG as usual reduced the mean arterial pressure.

These results indicate that SDG-induced fall in the blood pressure is partially mediated through blockade of angiotensin II receptor.

EXAMPLE 4

The effects of SDG on the arterial pressure of anesthetized spontaneous hypertensive rats (SHR) were investigated to determine (a) if it is effective in lowering blood pressure to the same extent as in normotensive Sprague-Dawley rats; (b) if it is effective when given by intraperitoneal route; (c) if the effect is dose-dependent.

Figure 15:
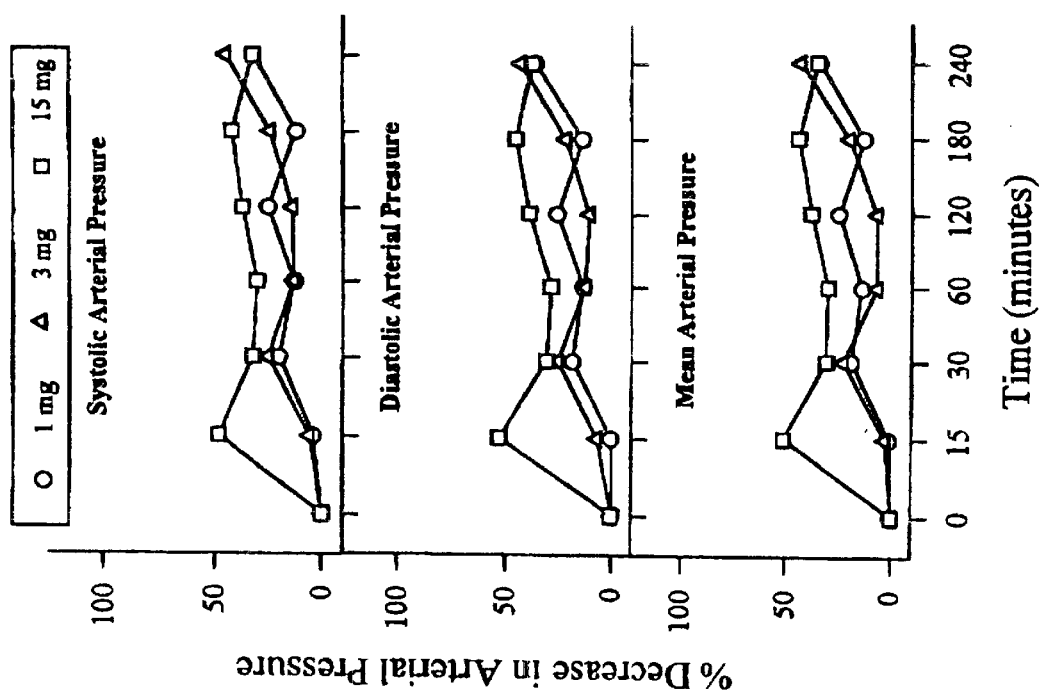
FIG. 15 is a graph showing the effects of intravenous administration of various doses (1 mg, 3 mg and 15 mg/kg body wt.) of SDG on the arterial pressures (systolic, diastolic and mean) in anesthetized spontaneous hypertensive rats observed for four hours; results are expressed as percent decrease.

(i) Effects of SDG in the doses of 1 mg, 3 mg and 15 mg/kg given intravenously were investigated on the blood pressures of anesthetized spontaneous hypertensive rats (SHR). The preliminary results are shown in FIG. 15. The maximum fall in the blood pressure occurred between 15 to 30 minutes of SDG administration after which the blood pressure tended to recover. However, the recovery was short lived. The percent decreases in blood pressures at 30 minutes after SDG were 19, 25 and 31 respectively with 1 mg, 3 mg and 15 mg/kg of SDG. At the end of 4 hours of SDG treatment, the percent decreases were 34, 43 and 36 respectively with 1 mg, 3 mg and 15 mg dose. The fall in the blood pressure initially (at 15 minutes) was maximum with high dose of SDG.

These results indicate that SDG has hypotensive effect, has long duration of action and the effect is dose-dependent. The effects appear to be greater in hypertensive than normotensive rats.

Figure 16:
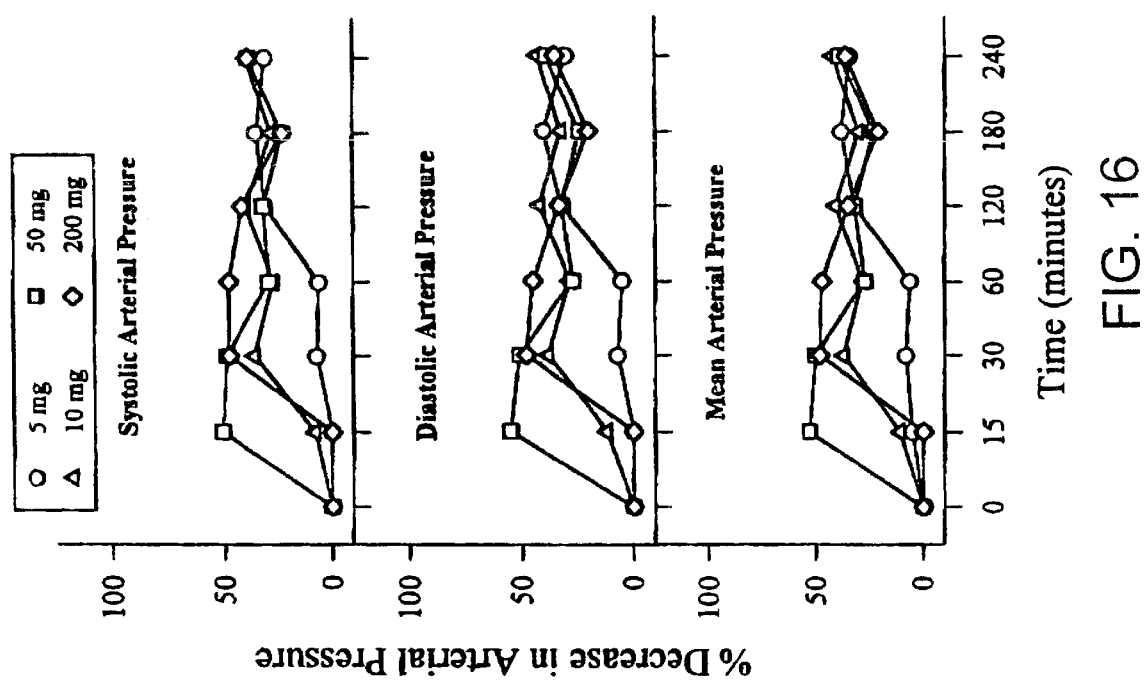
FIG. 16 is a graph showing the effects of intraperitoneal administration of various doses of SDG (5 mg, 10 mg, 50 mg and 200 mg/kg body wt.) on the arterial pressures (systolic, diastolic and mean) in anesthetized spontaneous hypertensive rats observed for four hours; results are expressed as percent decrease.

(ii) Effects of SDG in the doses of 5 mg, 10 mg, 50 mg and 200 mg/kg given intraperitoneally were investigated on blood pressure of anesthetized SHR for four hours. The preliminary results are shown in FIG. 16. The maximum fall in the blood pressure were approximately 7, 37, 50 and 48% respectively with 5 mg, 10 mg, 50 mg and 200 mg of SDG at 30 minutes. At the end of four hours of SDG administration the percent decreases in blood pressures were 31, 42, 39 and 37 respectively with these four doses of SDG.

These results indicate that SDG given intraperitoneally is hypotensive, has long duration of action, and its effect is dose-dependent.

Figure 17:
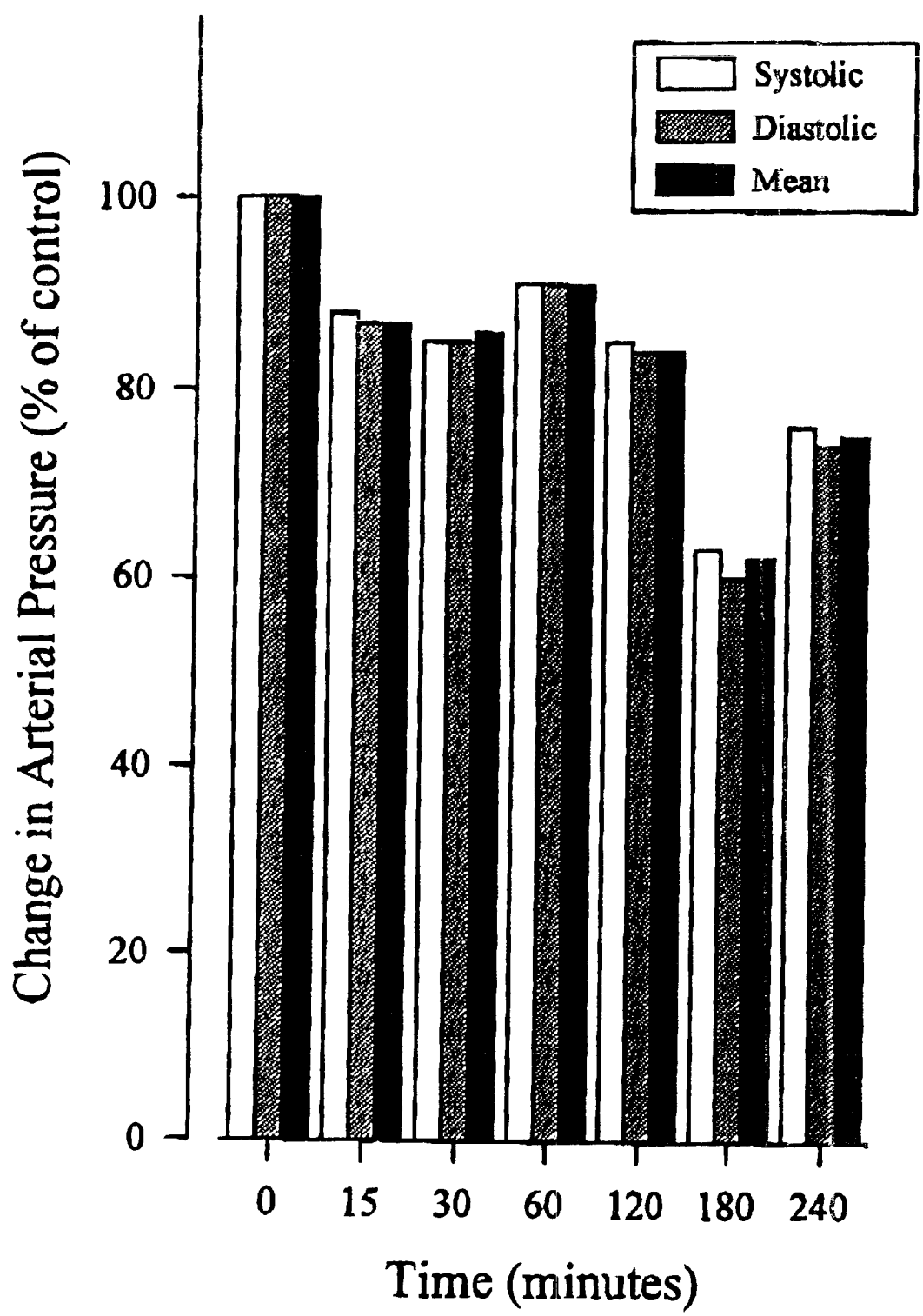
FIG. 17 is a graph showing the effects of oral administration of SDG (100 mg/kg body wt.) on the arterial pressures (systolic, diastolic and mean) in anesthetized spontaneous hypertensive rats observed for four hours; the results are expressed as percent change from control taken as 100%.

(iii) Effects of SDG (100 mg/kg body wt.) given orally were investigated on the blood pressure of anesthetized spontaneous hypertensive rats for four hours. The preliminary results are shown in FIG. 17. The blood pressures began falling at 15 minutes of SDG administration and maximum fall occurred after three hours. The decreases were of similar magnitude for systolic, diastolic and mean arterial pressures. The systolic, diastolic and mean arterial pressures respectively were 243 mmHg, 176 mmHg and 198 mmHg before administration of SDG. SDG reduced the blood pressure by approximately 25%.

These results indicate that SDG is effective in lowering lood pressure given orally.

What is claimed is:

1. A method for treating hypertension or for reducing or preventing development of elevated blood pressure which comprises administering to a patient an effective amount of secoisolariciresinol diglucoside (SDG) obtained from flaxseed and having a purity of at least 95%.

2. A method according to claim 1 wherein the SDG is administered in an amount of 10–30 mg/kg of body weight in a normotensive patient.

3. A method according to claim 1 wherein the SDG is administered in an amount of 1–15 mg/kg of body weight in a hypertensive patient.

* * * * *